(12) United States Patent
Wagner et al.

(10) Patent No.: US 6,485,745 B1
(45) Date of Patent: *Nov. 26, 2002

(54) SOLID ORAL DOSAGE FORMS OF VALSARTAN

(75) Inventors: Robert Frank Wagner, Neshanic Station, NJ (US); Yoshimitsu Katakuse, Hirakata (JP); Takashi Taike, Kobe (JP); Fujiki Yamato, Takarazuka (JP); Manfred Kohlmeyer, Basel (CH)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/920,159

(22) Filed: Aug. 1, 2001

Related U.S. Application Data

(63) Continuation of application No. 09/202,805, filed as application No. PCT/EP97/03172 on Jun. 18, 1997, now Pat. No. 6,294,197.

(30) Foreign Application Priority Data

Jun. 27, 1996 (GB) .............................. 9613470

(51) Int. Cl.⁷ ................................ A61K 9/20
(52) U.S. Cl. ....................... 424/465; 424/464; 424/489; 514/223.5; 514/223.2; 514/222.8
(58) Field of Search ................................ 424/465, 464, 424/479, 489; 514/772.5, 222.8, 223.5

(56) References Cited

U.S. PATENT DOCUMENTS

| | | | |
|---|---|---|---|
| 3,200,039 A | 8/1965 | Thompson, Jr. ............. | 167/82 |
| 4,353,887 A | 10/1982 | Hess et al. ..................... | 424/15 |
| 5,399,578 A | 3/1995 | Bühlmayer et al. ......... | 514/381 |
| 5,464,854 A | 11/1995 | dePadova .................... | 514/381 |
| 5,486,364 A | 1/1996 | King et al. .................. | 424/488 |
| 6,218,414 B1 * | 4/2001 | Nisato ......................... | 514/382 |

FOREIGN PATENT DOCUMENTS

| | | |
|---|---|---|
| DE | 2421 273 | 11/1974 |
| EP | 11 490 | 5/1980 |
| EP | 70 127 | 1/1983 |
| EP | 396 335 A | 11/1990 |
| WO | 93/15732 | 8/1993 |
| WO | 94 09778 | 5/1994 |
| WO | 95 24901 | 9/1995 |
| WO | 95 28927 | 11/1995 |
| WO | 95 29674 | 11/1995 |

OTHER PUBLICATIONS

"Hydrochlorothiazide"—Martindale 89 pp. 991–993.
"Innovatives Antihypertensives," Therapiewoche 36, pp. 1982–1985 (1996).
Chemical Abstracts 124:220073 (1996).
DIALOG: Derwent Drug File—Abstract AN:96–09445 (1996).
DIALOG: Drug Data Report—Abstract AN 185987 (1992).
DIALOG: JICST EPlus—Abstract AN:96A0157433 (1995).
EMBASE: Abstract 96015489 (1995).
EMBASE: Abstract 96–374183 (1996).
EMBASE: Abstract AN–97–027003 (1997).
Fujimura Y. et al., "Antihypertensive effect of a combination of Valsartan . . . ", Yakuri to Chiryo, vol. 23, No. 12, 1995, pp. 3241–3247.
Grun, A. et al., "A comparison of the efficacy and tolerability . . . ",European Heart Journal, vol. 161, No. Sup. (1995) p. 61.
Lachman, L. et al., "The Theory and Practice of Industrial Pharmacy," Lea & Febiger, 1986, pp. 318–320.
Markham, A., et al., "Valsartan: a review of its pharmacology and therapeutic use . . . ," DRUGS, vol. 54, No. 2, (1997) pp. 299–311.
TOXLIT: Abstract AN–96:69983 (1995).
Fujimura et al., "Antihypertensive Effect of a Combination of Valsartan and Hydrochlorothiazide, Nifedipine or Propranolol in Spontaneously Hypertensive Rats," Japan Pharmacol Ther, vol. 23(12), pp. 3241–3247 (1995). English Translation Included.

* cited by examiner

Primary Examiner—Thurman K. Page
Assistant Examiner—Liliana Di Nola-Baron
(74) Attorney, Agent, or Firm—Diana Tso

(57) ABSTRACT

The present invention is concerned with solid oral dosage forms of comprising
  a) an active agent selected from valsartan and optionally HCTZ , and
  b) Pharmaceutically acceptable additives suitable for the preparation of solid oral dosage forms by compression methods.

24 Claims, No Drawings

SOLID ORAL DOSAGE FORMS OF VALSARTAN

This application is a continuation of U.S. application Ser. No. 09/204,805, filed May 7,1999, now U.S. Pat. No. 6,294,197 which is a 371 of International Application PCT/EP97/03172, filed Jun. 18, 1997.

The invention relates to solid oral dosage forms containing valsartan, in particular solid oral dosage forms containing valsartan and hydrochlorothiazide (HCTZ) and a process of forming the same.

The angiotensin 11 receptor antagonist—Valsartan—is known to be effective in the treatment of congestive hear failure and reducing blood pressure irrespective of age, sex or race and is also well tolerated. Its combination with HCTZ is also known for the treatment of hypertension.

The oral administration of such pharmaceutical agents as tablets or capsules has rennin advantages over parenteral administration such as i.v. or i.m.: Diseases requiring treatment with painful injectable formulations are considered to be more serious than those conditions which can be treated with oral dosage forms. However, the major advantage with oral formulations is held to be their suitability for self administration whereas parenteral formulations have to be administered in moat cases by 2 physician or paramedical personnel.

However, valsartan is difficult to formulate and heretofore it has not been possible to make oral formulations in the form of tablets in a reliable and robust way.

Capsules are undesirable since large capsules must be used to accommodate effective amounts of active agent, which in the case of valsartan, is of low density and is therefore rather bulky.

We have now found a solid oral dosage form containing valsartan or a pharmaceutically acceptable salt thereof optionally in combination with HCTZ which can be produced according to a reliable and robust process, which solid oral dosage form is small relative to the amount of active agent used. Said solid oral dosage forms are smaller, for a given amount of active agent, than any known formulations of this active substance.

According to the invention there is provided a solid oral dosage form comprising
a) an active agent containing an effective amount of valsartan or a pharmaceutically acceptable salt thereof and
b) pharmaceutically acceptable additives suitable for the preparation of solid oral dosage forms by compression methods preferably wherein the active agent is present in an amount of more than 35% by weight, preferably more than 50% by weight based on the total weight of the solid oral dosage form. In particular, the amount of active agent may be present in an amount of from 45 to 65% by weight, e.g. 57 to 62% by weight.

Solid oral dosage forms according to the invention provide for the administration of the active substance in a smaller oral form than was heretofore possible for a given unit dose of active agent. Furthermore, the oral dosage forms obtained are stable both to the production process and during storage, e.g. for 2 years in conventional packaging, e.g. scaled aluminium blister packs.

By "effective amount" is meant the amount of active agent which halts or reduces the progress of the condition being treated or which otherwise completely or partly cures or acts palliatively on the condition. Such an amount can be easily determined by a person skilled in the art by routine experimentation and with no undue burden.

In a solid oral dosage form according to the invention wherein the active agent consists entirely of valsartan or a pharmaceutically acceptable salt thereof, it is preferred if the active agent is present in an amount of from 10 to 250 mg, more preferable 40 to 160 mg, most preferably 40 to 80 mg, e.g. 40, 80 or 160 mg.

The active agent valsartan is particularly suitable for combination with other active agents, e.g. HCTZ.

Accordingly, in an further embodiment of the invention there is provided a solid oral dosage form as hereinabove described additionally containing HCTZ as a component of the active agent.

It has been found that valsartan, or a pharmaceutically acceptable salt thereof, combined in a dose range from about 10 to 250 mg with hydrochlorothiazide in a dose range from about 6 to 60 mg, is suitable for more efficient treatment of hypertension. With these dose ranges of the combined active agents, valsartan is found to have a greater efficacy in reducing elevated blood pressure to normal levels than it would have if used at the same dose range in monotherapy. Moreover, when hydrochlorothiazide is being administered in combination with valsartan, the diuretic agent is more effective as compared to monotherapy at the dose range indicated. Particularly suitable is a dose range from about 50 and 100 mg valsartan or a pharmaceutically acceptable salt thereof and from about 10 to 30 mg hydrochlorothiazide. More preferred is a unit dose of about 80 mg valsartan and 12.5 mg or 25 mg of hydrochlorothiazide and 160 mg valsartan and 12.5 mg or 25 mg of hydrochlorothiazide. The weight ratio of valsartan or a pharmaceutically acceptable salt thereof to hydrochlorothiazide is from about 1:6 to about 42:1, more preferably 2:1 to 13:1, most preferably 2:1 to 10:1.

The present invention particularly relates to a solid oral dosage form, which contain as the active agent a)
a unit dose between about 10 and 254 mg, especially between about 54 and 100 mg, of valsartan or a pharmaceutically acceptable salt thereof; and
a unit dose between about 6 and 60 mg, especially between about 10 and 30 mg, of hydrochlorothiazide.

An especially preferred embodiment of the invention is a solid oral dosage form, which contain as the active agent a)
a unit dose of about 80 mg or 160 mg of valsartan or a pharmaceutically acceptable salt thereof; and
a unit dose of about 12.5 mg hydrochlorothiazide.

The preparation of valsartan is described in the U.S. Pat. No. 5,399,578 which is incorporated herein by reference. A pharmaceutically acceptable salt of valsartan can be prepared in a manner known per se. Thus for example, acid addition salts are obtained by treatment with an acid or a suitable ion exchange agent. Such salts can be convened to free acid in a conventional manner by treatment with a suitable basic agent.

Valsartan is preferably in its free form, that is, not in one of its salt forms.

Hydrochlorothiazide is a known therapeutic agent which is useful in the treatment of hypertension.

A solid oral dosage form according to the invention comprises additives conventional in the dosage form in question. Tabletting aids, commonly used in tablet formulation can be used and reference is made to the extensive literature on the subject, see in particular Fieldler's "Lexicon der Hilfstoffe", 4th Edition, ECV Aulendorf 1996 which is incorporated herein by reference. These include but are not limited to disintegrants, binders, lubricants, glidants, stabilising agents, fillers or diluents, surfactants and the like.

As disintegrants one can particularly mention CMC—Ca, CMC—Na, crosslinked PVP (Crospovidone, Polyplasdone of Kollidon XL), Alginic acid, radium alginate and guar gum, most preferably crosslinked PVP, Crospovidone, crosslinked CMC and Ac—Di—Sol.

As binders one can particularly mention starches, e.g. potato starch, wheat starch, corn starch, microcrystalline cellulose, e.g. products known under the registered trade marks Avicel, Filtrak, Heweten or Pharmacel, hydroxypropyl cellulose, hydroxyethyl cellulose and hydroxypropylmethyl cellulose, e.g. hydroxypropyl cellulose having a hydroxypropyl content of 5 to 16% by weight and a Mw of from 80,000 to 1,150,000, more particularly 140,000 to 850,000.

As glidants one can mention in particular colloidal silica, e.g. Aerosil, magnesium trisilicate, powdered cellulose, starch, talc and tribasic calcium phosphate.

As fillers or diluents one can mention confectioner's sugar, compressible sugar, dextrates, dextrin, dextrose, lactose, mannitol, microcellulose, in particular having a density of about 0.45 g/cm$^3$, e.g. Avicel, powdered cellulose, sorbitol, sucrose and talc.

As lubricants one can mention in particular Mg, Al or Ca stearate, PEG 4000–8000 and talc.

One or more of these additives can be selected and used by the skilled artisan having regard to the particular desired properties of the solid oral dosage form by routine experimentation and without any undue burden.

The amount of each type of additive employed, e.g. glidant, binder, disintegrant, filler or diluent and lubricant may vary within ranges conventional in the art. Thus for example, the amount of glidant may vary within a range of from 0.1 to 10% by weight, in particular 0.1 to 5% by weight, e.g. 0.1 to 0.5% by weight; the amount of binder may vary within a range of from about 10 to 45% by weight, e.g. 20 to 30% by weight; the amount of disintegrant may vary within a range of from 2 to 20% by weight, e.g. 15% by weight; the amount of filler or diluent may vary within a range of from 15 to 40% by weight; whereas the amount of lubricant may vary within a range of from 0.1 to 5.0% by weight.

It is a characteristic of the present solid oral dosage forms that they contain only a relatively small amount of additives given the high content of active agent. This enables the production of physically small unit dosage forms. The total amount of additives in a given unit dosage may be about 65% or less by weight based on the total weight of the solid oral dosage form, more particularly about 50% or less. Preferably the additive content is in the range of about 35 to 55% by weight, more particularly 45 to 55% by weight, e.g. 38 to 43% by weight.

The absolute amounts of each additive and the amounts relative to other additives is similarly dependent on the desired properties of the solid oral dosage form and tray also be chosen by the skilled artisan by routine experimentation without undue burden. For example, the solid oral dosage form may be chosen to exhibit accelerated and/or delayed release of the active agent with or without quantitative control of the release of active agent.

Thus, where accelerated release is desired, e.g. about 90% release within a ten minute, more particularly a five minute period, a disintegrant such as crosslinked polyvinyl pyrrolidone, for example those products known under the registered trade marks Polyplasdone®XL or Kollidon®CL, in particular having a molecular weight in excess of 1,000,000, more particularly having a particle size distribution of less than 400 microns or less than 74 microns, or reactive additives (effervescent mixtures) that effect rapid disintegration of the tablet in the presence of water, for example so-called effervescent tablets that contain an add in solid form, typically citric add, which acts in water on a base containing chemically combined carbon dioxide, for example sodium hydrogencarbonate or sodium carbonate, and releases carbon dioxide could be used.

Whereas if delayed release is desired one can employ pellet coating technology, wax matrix systems, polymer matrix tablets or polymer coatings conventional in the art.

Quantitative control of the release of the active agent can be achieved by conventional techniques known in the art. Such dosage forms are known as oral osmotic systems (OROS), coated tablets, matrix tablets, press-coated tablets, multilayer tablets and the like.

In a solid oral dosage form wherein the active agent consist entirely of valsartan or a pharmaceutically acceptable salt thereof, preferred additives are microcrystalline cellulose, hydroxypropylcellulose, carboxymethylcellulose (CMC) or CMC—Ca, Mg, Ca or Al stearate, anhydrous colloidal silica and talc. The amounts of additive employed will depend upon how much active agent is to be used. The stearate, e.g. Mg stearate is preferably employed in amounts of 1.0 to 5.0% by weight, e.g. 1.5% to 3.0% by weight. Whereas the silica is preferably employed in an amount of from 0.5 to 10% by weight.

In a solid oral dosage form wherein the active agent consists of a combination of both valsartan or a pharmaceutically acceptable salt thereof and HCTZ it is preferred to employ additives selected from any of those additives recited in the previous paragraph and crosslinked polyvinylpyrollidone. The stearate is preferably employed in an amount of from 1 to 5% by weight, e.g. 3%. The cellulose material, e.g. microcrystalline cellulose is preferably present in an amount of 10 to 30%, e.g. 21%. The silica is preferably present in an amount of from 0.5 to 10%, e.g. 1% by weight. The crosslinked polyvinylpyrolidone is preferably present in an amount of from 10 to 20%, e.g. about 13% by weight. Particularly preferred solid oral dosage forms contain as additives microcrystalline cellulose and crosslinked polyvinylpyrrolidone (PVP).

The solid oral dosage forms according to the present invention may be in the form of dragées in which case the solid oral dosage form is provided with a coating typically a sugar, shellac or other film coating entirely conventional in the art. Attention is drawn to the numerous known methods of coating employed in the art, e.g. spray coating in a fluidized bed, e.g. by the known methods using apparatus available from Aeromatic, Glatt, Wurster or Hüttlin, in a perforated pan by the Accela Cota method, or to the submerged sword coating method. The additives commonly used in confectioning are employed in such methods.

The solid oral dosage forms of the present invention are useful for lowering the blood pressure, zither systolic or diastolic or bath. The conditions for which the instant invention is useful include, without limitation, hypertension (whether of the malignant, essential, reno-vascular, diabetic, isolated systolic, or other secondary type), congestive heart failure; angina (whether stable or unstable), myocardial infarction, artherosclerosis, diabetic nephropathy, diabetic cardiac myopathy, renal insufficiency, peripheral vascular disease, left ventricular hypertrophy, cognitive dysfuntion (such as Alzheimer's) and stroke.

The exact dose of active agent and the particular formulation to be adminstered depend on a number of factors, e.g. the condition to be treated, the desired duration of the treatment and the rate of release of the active agent. For example, the amount of the active agent required and the release rate thereof may be determined on the basis of known in vitro or in vivo techniques, determining how long a particular active agent concentration in the blood plasma remains at an acceptable level for a therapeutic effect.

The invention provides in another of its aspects a process of making a solid oral dosage form as hereinabove described. Such solid oral dosage form may be produced by working up components a) and b) defined hereinabove in appropriate amounts, to form unit dosage forms.

In a preferred embodiment there is provided a process of making the solid oral dosage forms as hereinabove described comprising the steps of i) grinding the active agent and pharmaceutically acceptable additives, ii) subjecting a mixture of the grand active agent and additives to compression to form a coprimate iii) converting the coprimate to form a granulate and iv) compressing the granulate to form the solid oral dosage form.

The process is carried out in the absence of water, i.e. it is a dry compression method The process may be carried out under ambient conditions of temperature and humidity; it is not necessary to ensure that the process is carried out in a dry atmosphere.

The initial grinding step i) may be carried out according to conventional milling methods or micronisation methods. The active agent and the additives can be milled either individually or together to particle sizes from about 0.1 $\mu$ to about 200 $\mu$, preferably 1.0 $\mu$ to 100 $\mu$. At least 90% of the crystals of both the active agent and the additives are present in these ranges. Particles of this size are obtained by conventional comminution methods, e.g. grinding to an air jet mill, hammer and screen mill, fine impact mill, ball mill or vibrator mill.

Micronisation is preferably effected by known methods using an ultrasonic disintegrator, e.g. of the BRANSON Sonifier type, or by stirring a suspension with 2 high spud agitator, for example with a stirrer of the HOMOREX type.

The ground particles may optionally at this stage be sieved and mixed according to known methods.

Compression to form a coprimate requires the compaction of the dry ground components. Compaction may be carried out using a slugging technique or preferably, roller compaction. Roller compaction apparatus is conventional and essentially utilises two rollers which roll towards each other. A hydraulic ram forces one of the rollers against the other to exert a compacting force against the ground particles fed into the roller compactor via a screw conveyor system.

A compaction force of between 25 and 65 kN is preferably used. Within this range of compaction forces it has surprisingly been found that for each particular formulation a minimum compaction force should be used in order to obtain a solid oral dosage form wherein the granulate disintegrates into discrete primary particles at a desirable rate, e.g. disintegration occurs approximately six times faster for a solid oral dosage form compressed above a minimum compaction force. Such a rapind disintegration rate is unusual for tablets and is similar to the disintegration rate of a capsule formulation. The particular minimum compaction force is dependent on the active agent content in any given formulation and therefore also depends on the amount and nature of the additives present.

A solid oral dosage form containing an active agent consisting of 80 mg valsartan and 12.5 mg HCTZ, and appropriate additives in appropriate quantities is preferably made by a process wherein the compaction force used to produce the coprimate is at least 30 kN. Appropriate additives in appropriate quantities for this active agent may be 31.5 mg microcrystalline cellulose, 1.5 mg anhydrous colloidal silica, 4.5 mg magnesium stearate and 20 mg crosslinked PVP.

A solid oral dosage form comprising a unit dose of 160 mg valsartan and 12.5 mg HCTZ, and appropriate additives in appropriate quantities is preferably made by a process wherein the compaction force used to produce the coprimate is at least 25 kN. Appropriate additives in appropriate quantities for this active agent may be 75.5 mg microcrystalline cellulose, 3.0 mg anhydrous colloidal silica, 9.0 mg magnesium stearate and 40 mg crosslinked PVP.

Given this information, the skilled addressee would clearly be able to determine the minimum compaction force for other formulations using routine experimentation and without undue burden.

The roller speed is set at between 1 and 15 rpm and is preferably 1.3 to 7.5 rpm. After passing through the rollers the compacted mass (the coprimate) resembles a thin ribbon in segments.

The coprimate may be screened and or milled to produce the granulate. Screening in its simplest form involves the passing of the coprimate emerging from the rollers through a seive under mechanical pressure. More preferably, the coprimate is screened using an oscillating mill, e.g. a MGI 624 Frewitt (Key International Inc.).

The granulate thus formed has a rather wide particle size distribution e.g. from 9 to 340 microns. At this stage of the roller compaction process it is conventional to sort the under-sized and over-sized particles and remove them from the granulate for recycling or recirculation. Thus removed the over- and under-sized particles art typically compacted an additional one or more times in order to obtain the desired particle size distribution of the granulate. Such a process is time consuming and therefore increases the cost of manufacture of solid oral dosage forms. Furthermore, the additional passes through the roller compactor under such high compaction forces can have deleterious effects on the active agent and also render the granulate less suitable for compression into the solid oral dosage form.

It has been found however, that the granulate first emerging from the roller compactor after screening or milling and containing both over- and under-sized particles can in fact be compressed to form solid oral dosage forms without affecting the properties of the solid oral dosage form.

The compression of the granulates to tablet cores can be carried out in a conventional tabletting machine, e.g. in an EK-0 Korsch eccentric tabletting machine or a rotary compression machine, preferably at a compression greater than 2 kN. The tablet cores may vary in shape and be, for example, round, oval, oblong, cylindrical or any other suitable shape, and may also vary in size depending on the concentration of the therapeutic agents. A characteristic of tablets according to the invention is their small size having regard to the amount of active agent contained therein.

In a preferred embodiment of the invention tablets obtained by the compression method described above are slightly oval. The edges of the tablets may be bevelled or rounded.

In a particularly preferred embodiment of the invention a solid oral dosage form is compressed in the form of a tablet having an oblong shape in which the ratio of dimensions length:width:height is 2.5–5.0; 0.9–2.0; 1.0 and preferably in which the base and top face of the tablet independently of one another are planar or convexly curved about the longitudinal axis; the side facts are planar, the end faces can be of any shape and the edges are optionally bevelled or rounded.

In a particularly preferred embodiment of the invention a solid oral dosage form is compressed, from the granulate, in the form of a tablet of oblong shape in which the length is approximately 10.0 to 11.0 mm, the width approximately 5.0 to 6.0 mm and the height approximately 3.0 to 4.0 mm.

In another particularly preferred embodiment of the invention a solid oral dosage form is compressed from granulates in the form of a tablet of oblong shape in which the length is approximately 15.0 to 16.0 mm, the width approximately 6.0 to 7.0 mm and the height approximately 3.5 to 5.0 mm.

In yet another preferred embodiment of the invention there is provided a tablet which is essentially disc-shaped with the upper and lower faces having a slightly convex surface. Preferably the tablet has a diameter of about 8 to 8.5 mm and a depth of about 3 to 3.5 mm, or a diameter of about 16 mm and a depth of about 6 mm. The tablets may occupy a volume from about 0.1 $cm^3$ to about 0.45 $cm^3$, more particularly 0.2 to 0.3 $cm^3$, e.g about 0.125 $cm^3$ or 0.25 $cm^3$.

They may furthermore be transparent, colourless or coloured and also marked so as to impart to this product an individual appearance and to make them instantly recognizable. The use of dues can serve to enhance the appearance as well as to identify the compositions. Dyes suitable for use in pharmacy typically include carotinoids, iron oxides or chlorophyll.

There now follows a series of examples which serve to illustrate the invention.

EXAMPLE 1

Formula

| | |
|---|---|
| valsartan | 80.0 mg (53.3%) |
| hydrochlorothiazide | 12.5 mg (8.3%) |
| colloidal anhydrous silica AEROSIL | 1.5 mg (1.0%) |
| microcrystalline cellulose AVICEL | 31.5 mg (21.0%) |
| polyvinylpyrrolidone CROSPOVIDONE | 20.0 mg (13.3%) |
| magnesium stearate | 4.5 mg (3.0%) |
| | 150.0 mg |

Method

The components except for a portion of the magnesium stearate are blended in a container mixer. The blended material is sieved and pre-blended for an additional period of time in a container mixer. The blended material is compacted using a roller compactor (Bepex Pharmapaktor L 200/50 P, Hosokawa Micron Group) by applying a compaction force of 25–65 kN and a roller speed of 1.3–7.5 rpm. The compacted material is sieved again and the remaining portion of the magnesium stearate is added and final blended in a container mixer. Then 150 mg of the homogenous mixture is compressed into tablets using ovaloid punches (10×5.2 mm). The tablets obtained have a length of 10.0–10.2 mm, a width of 5.2–5.4 mm and a height of 3.3–3.9 mm.

EXAMPLE 1a

A solid oral dosage form prepared according to Example 1 is coated with a film coating formulation:

| | |
|---|---|
| Cellulose H-P-M683 | 2.76 mg |
| Fe Oxide (Yellow) 17268 | 0.025 |

| -continued | |
|---|---|
| Fe Oxide (Red) 17266 | 0.025 |
| PEG 8000 (flakes) | 0.5 |
| Talc PH | 2.0 |
| Titanium dioxide PH | 0.7 |
| Deionised water | 2.5 |
| Ethanol + 5% Isopropyl alcohol | 20.0 |

Method

The PEG and cellulose are dissolved in the deionised water. The remaining components are suspended in the resulting solution. A spray coater apparatus (Driacoater DRC-500, Powrex Ltd) is charged with the solid oral dosage form of Example 1. The coating formulation is sprayed into the solid oral dosage form relating in the apparatus at 6–12 rpm. Spray pressure is 1.9–2.2 Kg/$cm^2$ and the spray rate is 5.9–7.9 g/min.

Thereafter the coated solid oral dosage form is dried in the coater apparatus at a temperature of 40° C. until a moisture content in the coated solid oral dosage form is less than 2.5% by weight.

The tablets obtained have a length of 10.1–10.3 mm, a width of 5.3–5.5 mm and a height of 3.4–4.0 mm

EXAMPLE 2

Formula

| | |
|---|---|
| valsartan | 160.0 mg (53.3%) |
| hydrochlorothiazide | 12.5 mg (8.3%) |
| colloidal anhydrous silica AEROSIL | 3.0 mg (1.0%) |
| microcrystalline cellulose AVICEL | 75.5 mg (21.0%) |
| polyvinylpyrrolidone CROSPOVIDONE | 40.0 mg (13.3%) |
| magnesium stearate (FAC I) | 9.0 mg (3.0%) |
| | 300.0 mg |

A 300.0 mg tablet is formed according to the method described in Example 1. The tablets obtained have a length of 15.0–15.2 mm, a width of 6.0–6.2 mm and a height of 3.9–4. mm.

EXAMPLE 2a

A solid oral dosage form according to Example 2 is coated with a composition (see formulation below) according to the methodology of Example 1a.

Formulation

| | |
|---|---|
| Cellulose H-P-M683 | 5.51mg |
| Fe Oxide (Red) 17266 | 0.75 |
| PEG 8000 (flakes) | 1.0 |
| Talc PH | 3.99 |
| Titanium dioxide PH | 0.75 |
| Deionised water | 5.0 |
| Ethanol + 5% Isopropyl alcohol | 40.0 |

The tablets obtained have a length of 15.1–15.3 mm, a width of 6.1–6.3 mm and a height of 4.0–4.8 mm.

EXAMPLE 3

Formula

| | |
|---|---|
| valsartan | 80.0 mg (40%) |
| AEROSIL 200 | 10.0 mg (5%) |
| L-HPC* L-11 | 87.0 mg (43%) |
| Magnesium Stearate | 3.0 mg (1.5%) |
| AVICEL PH-301 | 10.0 mg (5%) |
| L-HPC* L-21 | 5.0 mg (2.5%) |
| AEROSIL 200 | 1.0 mg (0.5%) |
| Talc | 2.0 mg (1.0%) |
| Magnesium Stearate | 2.0 mg (1.0%) |
| | 200.0 mg |

*hydroxypropyl cellulose

Method

The components (above the line) are blended in a container mixer. The blended material is sieved and pre-blended for an additional period of time in a container mixer. The blended material is compacted using a roller compactor (Bepex Pharmapaktor L 200/50 P, Hosokawa Micron Group) by applying a compaction force of 25–65 kN and a roller speed of 1.3–7.5 rpm. The compacted material is sieved again and the components below the line are added and final blended in a container mixer. Then 200 mg of the homogenous mixture is compressed into tablets using ovaloid punches (10×5.2 mm). The tablets obtained have a diameter of 8.5 mm and a thickness of 3.9 mm.

EXAMPLE 3A

Film Coating

| | |
|---|---|
| Titanium dioxide | 1.00 mg |
| TC-5R* | 3.68 mg |
| PEG 6000 | 0.66 mg |
| Talc | 2.66 mg |
| | 8.00 mg |

*= hydroxypropylmethyl cellulose.

Method

The film coating is applied to the solid oral dosage form of Example 3 according to the methodology of Example 1A.

The coated tablet has a diameter of 8.6 mm and a thickness of 4.0 mm.

What is claimed is:

1. A compressed solid dosage form comprising:
   (a) an active agent comprising an effective amount of valsartan or a pharmaceutically acceptable salt thereof; and,
   (b) at least one pharmaceutically acceptable additive;
   wherein the active agent is present in an amount of more than 35% by weight based on the total weight of the compressed solid dosage form and wherein said dosage form exhibits accelerated release of the active agent.

2. The compressed solid dosage form according to claim 1 wherein the accelerated release constitutes about 90% release within a 10 minute period.

3. The compressed solid dosage form according to claim 1 wherein the additive is microcrystalline cellulose, cross-linked polyvinyl pyrrolidone, pregelatinized starch or hydroxypropyl cellulose.

4. The compressed solid dosage form according to claim 1, wherein the additive is an acid in a solid form.

5. The compressed solid dosage form according to claim 1, wherein the additive is citric acid.

6. A compressed solid dosage form comprising an active agent comprising an effective amount of valsartan or a pharmaceutically acceptable salt thereof an effective amount of HCTZ; and, at least one pharmaceutically acceptable additive wherein the active agent is present in an amount of more than 35% by weight based on the total weight of the compressed solid dosage form and wherein said dosage form exhibits accelerated release of the active agent.

7. The compressed solid dosage form according to claim 6 wherein the accelerated release constitutes about 90% release within a 10 minute period.

8. The compressed solid dosage form according to claim 6 wherein the additive is microcrystalline cellulose, cross-linked polyvinyl pyrrolidone, pregelatinized starch or hydroxypropyl cellulose.

9. The compressed solid dosage form according to claim 6 wherein the additive is an acid in solid form.

10. The compressed solid dosage form according to claim 6 wherein the additive is citric acid.

11. A compressed solid dosage form comprising;
    (a) an active agent comprising an effective amount of valsartan or a pharmaceutically acceptable salt thereof; and,
    (b) at least one pharmaceutically acceptable additive;
    wherein the active agent is present in an amount of more than 35% by weight based on the total weight of the compressed solid dosage form, and wherein said damage form exhibits delayed release of the active agent.

12. The solid dosage form according to claim 11 wherein the additive is hydroxypropyl methylcellulose.

13. A compressed solid dosage form comprising an active agent comprising an effective amount of valsartan or a pharmaceutically acceptable salt thereof; an effective amount of HCTZ; and, at least one pharmaceutically acceptable additive wherein the active agent is present in an amount of more than 35% by weight based on the total weight of the compressed solid dosage form and wherein said dosage form exhibits delayed release of the active agent.

14. The solid dosage form according to claim 13 wherein the additive is hydroxypropyl methylcellulose.

15. A method of treating hypertension, congestive heart failure, angina, myocardial infarction, arteriosclerosis, diabetic nephropathy, diabetic cardiac myopathy, renal insufficiency, peripheral vascular disease, stroke, left ventricular hypertrophy, cognitive dysfunction, headache, or chronic heart failure, wherein the method comprises administering a compressed solid dosage form as defined in claim 1 to a subject in need of such treatment.

16. A method of treating according to claim 15 wherein the compressed solid dosage form is orally administered to the subject.

17. A method of treating hypertension, congestive heart failure, angina, myocardial infarction, arteriosclerosis, diabetic nephropathy, diabetic cardiac myopathy, renal insufficiency, peripheral vascular disease, stroke, left ventricular hypertrophy, cognitive dysfunction, headache, or chronic heart failure, wherein the method comprises administering a compressed solid dosage form as defined in claim 6 to a subject in need of such treatment.

18. A method of treating according to claim 17 wherein the compressed solid dosage form is orally administered to the subject.

19. A method of treating hypertension, congestive heart failure, angina, myocardial infarction, arteriosclerosis, diabetic nephropathy, diabetic cardiac myopathy, renal insufficiency, peripheral vascular disease, stroke, left ventricular hypertrophy, cognitive dysfunction, headache, or chronic heart failure, wherein the method comprises administering a compressed solid dosage form as defined in claim 11 to a subject in need of such treatment.

20. A method of treating according to claim 19 wherein the compressed solid dosage form is orally administered to the subject.

21. A method of treating hypertension, congestive heart failure, angina, myocardial infarction, arteriosclerosis, diabetic nephropathy, diabetic cardiac myopathy, renal insufficiency, peripheral vascular disease, stroke, left ventricular hypertrophy, cognitive dysfunction, headache, or chronic heart failure, wherein the method comprises administering a compressed solid dosage form as defined in claim 13 to a subject in need of such treatment.

22. A method of treating according to claim 21 wherein the compressed solid dosage form is orally administered to the subject.

23. The compressed solid dosage form according to claim 6 wherein the accelerated release constitutes about 90% release within a 5 minute period.

24. The compressed solid dosage form according to claim 6 wherein the accelerated release constitutes about 90% release within a 5 minute period.

* * * * *

UNITED STATES PATENT AND TRADEMARK OFFICE
CERTIFICATE OF CORRECTION

PATENT NO.     : 6,485,745 B1                                           Page 1 of 1
DATED          : November 26, 2002
INVENTOR(S)    : Wagner et al.

It is certified that error appears in the above-identified patent and that said Letters Patent is hereby corrected as shown below:

Title page,
Item [63], should read:
-- Related U.S. Application Data
[63] Continuation of application No. 09/202,805, filed on May 7, 1999, now Pat. No. 6,294,197, which is a 371 of International Application PCT/EP97/03172, filed on June 18, 1997. --.

Column 1,
Line 5, should read: -- No. 09/202,805, filed May 7, 1999, now U.S. Pat. No. 6,294,197 --.

Column 10,
Line 27, should read: -- compressed solid dosage form, and wherein said dosage --.

Signed and Sealed this

Twenty-fifth Day of November, 2003

JAMES E. ROGAN
*Director of the United States Patent and Trademark Office*